(12) United States Patent
Chang et al.

(10) Patent No.: US 10,932,704 B2
(45) Date of Patent: Mar. 2, 2021

(54) DEVICE AND METHOD FOR MEASURING BLOOD OXYGEN LEVEL AND/OR DETECTING BRAIN HEMATOMA

(71) Applicant: MacKay Memorial Hospital, Taipei (TW)

(72) Inventors: Wen-Han Chang, Taipei (TW); Chih-Wei Lu, New Taipei (TW)

(73) Assignee: MACKAY MEMORIAL HOSPITAL, Taipei (TW)

( * ) Notice: Subject to any disclaimer, the term of this patent is extended or adjusted under 35 U.S.C. 154(b) by 534 days.

(21) Appl. No.: 15/526,004

(22) PCT Filed: Nov. 16, 2015

(86) PCT No.: PCT/CN2015/094690
§ 371 (c)(1),
(2) Date: May 11, 2017

(87) PCT Pub. No.: WO2016/074648
PCT Pub. Date: May 19, 2016

(65) Prior Publication Data
US 2017/0319116 A1    Nov. 9, 2017

Related U.S. Application Data

(60) Provisional application No. 62/080,038, filed on Nov. 14, 2014.

(51) Int. Cl.
*A61B 5/1455* (2006.01)
*A61B 5/00* (2006.01)

(52) U.S. Cl.
CPC ........ *A61B 5/14551* (2013.01); *A61B 5/0059* (2013.01); *A61B 5/14553* (2013.01);
(Continued)

(58) Field of Classification Search
CPC . A61B 5/1455; A61B 5/14551; A61B 5/0059; A61B 5/14553; A61B 5/6803; A61B 5/4064; A61B 5/7235
See application file for complete search history.

(56) References Cited

U.S. PATENT DOCUMENTS 4,281,645 A * 8/1981 Jobsis .................. A61B 5/0059
600/324
5,954,053 A * 9/1999 Chance ................ A61B 5/0059
600/310

(Continued)

*Primary Examiner* — Daniel L Cerioni
*Assistant Examiner* — Avery M Foley

(57) ABSTRACT

A device for measuring brain oxygen level of a subject, including a probe (210) and a detecting means (220), which are respectively coupled to a processor (230). According to the example, the probe (210) includes three light sources (215a, 215b, 215c) that simultaneously emit the first, second, and third NIR wavelengths across the brain of the subject. The first NIR wavelength is the isosbestic wavelength for oxy-hemoglobin (HbO2) and deoxy-hemoglobin (Hb), the second NIR wavelength is shorter than the first NIR wavelength, and the third NIR wavelength is longer than the first NIR wavelength. The detecting means (220) includes a first, second and third detectors (221, 222, 223) for respectively detecting the NIR intensities of the first, second and third NIR wavelengths traveled across the brain. The processor (230) is configured to determine blood oxygen level based on the measured NIR intensities of the first, second and third NIR wavelengths by use of build-in algorithm derived from Beer-Lambert Law. And method of detecting brain hematoma of a subject by use of the present device.

9 Claims, 15 Drawing Sheets

(52) U.S. Cl.
CPC .......... *A61B 5/6803* (2013.01); *A61B 5/4064* (2013.01); *A61B 5/7235* (2013.01)

(56) References Cited

U.S. PATENT DOCUMENTS

| | | | | |
|---|---|---|---|---|
| 2002/0033454 A1* | 3/2002 | Cheng | ................ | A61B 5/14546 |
| | | | | 250/339.12 |
| 2007/0106172 A1* | 5/2007 | Abreu | ................... | A61B 5/0002 |
| | | | | 600/549 |
| 2008/0139908 A1* | 6/2008 | Kurth | ................. | A61B 5/14553 |
| | | | | 600/340 |
| 2009/0281403 A1* | 11/2009 | Benni | ............... | A61B 5/14553 |
| | | | | 600/331 |
| 2011/0046491 A1* | 2/2011 | Diamond | ............ | A61B 5/0073 |
| | | | | 600/473 |
| 2011/0066050 A1* | 3/2011 | Moon | ................. | A61B 5/0006 |
| | | | | 600/509 |
| 2012/0230918 A1* | 9/2012 | Dobosz | .............. | A61B 3/1241 |
| | | | | 424/9.6 |
| 2013/0090541 A1* | 4/2013 | MacFarlane | ....... | A61B 5/14553 |
| | | | | 600/328 |
| 2013/0225955 A1* | 8/2013 | Schenkman | ....... | A61B 5/14551 |
| | | | | 600/328 |
| 2017/0231490 A1* | 8/2017 | Toth | ........................ | A61B 5/40 |
| | | | | 600/558 |

* cited by examiner

DEVICE AND METHOD FOR MEASURING BLOOD OXYGEN LEVEL AND/OR DETECTING BRAIN HEMATOMA

CROSS REFERENCE

This application claims priority from U.S. provisional patent application 62/080,038, filed on November 14, the content of which is incorporated herein by reference.

BACKGROUND OF THE INVENTION

1. Field of the Invention

The present disclosure in general, relates to the determination of brain oxygen level and the detection of brain hematoma. More particularly, the present disclosure relates to devices and methods for measuring the brain oxygen level and/or detecting the brain hematoma based on relative hemoglobin saturation measured at multiple sites of a subject using near infrared (NIR) wavelengths.

2. Description of Related Art

One of the most important principles for the initial resuscitation of a head trauma patient is to promptly identify and surgically evacuate traumatic intracranial hematomas. Hematoma is a condition by which blood accumulates outside blood vessel generally as a result of a hemorrhage or trauma. During the resuscitation, time is crucial as the expanding mass lesion can cause death from brainstem compression or cause ischemic injury of brain. It has been generally accepted that a delay of more than 4 hours between brain injury and the evacuation of hematoma would increase mortality and worsen outcome in survivors.

Several diagnostic methods have been developed to identify and localize traumatic intracranial hematomas, such as, computed tomography (CT), magnetic resonance imaging (MRI), X-radiation (X-ray), infrascan, and micropower impulse radar (MIR). However, each of these techniques has its own limitation when it comes to determine brain hematoma.

CT scanning, which provides 3D isotropic imaging for the damage sites, possesses the ability to image bone, soft tissue, and blood vessels all at the same time. However, the efficacy of a normal CT is usually limited by several drawbacks: (1) long preparation and examination time; (2) failure to accurately distinguish hematoma from hydrocephalus; (3) discontinuous monitoring; (4) failure to exclude underlying injury, such as, ischemia and hypoxia; (5) poor visualization in brainstem and posterior fossa; (6) radiation exposure; and (7) the possibility of contrast-induced allergy or nephropathy. All of which impedes the clinical application of CT.

MRI, an imaging technique not involving the exposure to ionizing radiation, provides a sensitive means to detect and evaluate damage in brainstem and stroke at a very early stage by mapping the motion of water molecules in the tissue. Nevertheless, the clinical application of MRI might be restricted due to several reasons as indicated below. First, the presence of an implant or other metallic object within the subject would render it difficult to obtain clear images. Second, patients having acute injury in general is not in a condition for MRI imaging, for traction devices and other life support equipment must be kept away from the area to be imaged. Third, the process is time consuming and the results may not be immediately available. Further, similar to the concerns in using CT, the contrast employed in either imaging process might induce allergy or nephropathy to the patients.

X-ray is a form of electromagnetic radiation. It takes only few seconds to complete the image scanning. The major limitation of X-ray imaging is its incapability of changing imaging plane, thus fails to provide detailed stereoscopic information via its 2D images. In addition, X-ray might cause defects and/or diseases due to its destructing effects on DNA.

Infrascan is a technology that uses NIR to screen patient with head trauma. The diagnosis is made based on the comparative data of optical density between contralateral sides of the head. Accordingly, an inherent inaccurate diagnosis exists in the condition when a bilateral hematoma occurs.

MIR technology is based on the emission of extremely short duration electromagnetic impulses that penetrate the human body. Unlike ultrasound or other electromagnetic techniques, MIR can operate well through the skull, which is of great importance for intracerebral as well as epidural and subdural hematomas. However, similar to the concerns in using infrascan, successful operation of MIR requires the inherent bilateral symmetry of the brain, as well as differential analysis of the baseline or pre-injury scan, so as to identify abnormalities in brain. Accordingly, MIR can only be used to detect unilateral hematoma, but not bilateral hematoma.

In view of the foregoing, there exists in the art a need of an improved device and/or method that may continuously monitor the changes in blood oxygen level, so as to facilitate an early detection of brain hematoma, particularly, the bilateral hematoma.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, disclosure herein features a device and the use thereof for measuring brain oxygen level and/or monitoring brain hematoma in a subject.

In the first aspect, the present disclosure is directed to a device that is used to measure brain oxygen level and/or monitor a brain hematoma in a subject. The device comprises, a probe comprising a first, a second, and a third light sources configured to respectively emit a first, a second, and a third near infrared (NIR) wavelengths across the brain of the subject, wherein the first NIR wavelength is about 790 nm to 810 nm, the second NIR wavelength is about 650 nm to 790 nm, and the third NIR wavelength is about 810 nm to 1,000 nm;

a detecting means comprising a first, a second, and a third NIR detectors, wherein each of the NIR detectors is configured to respectively measure the first, the second, and the third intensities of the first, second, and third NIR wavelengths after being transmitted across the brain of the subject; and a processor that is coupled to the probe and the detecting means, and is configured to determine the brain oxygen level or analyze the brain hematoma based on the first, second, and third intensities detected by the NIR detectors.

According to one embodiment of the present disclosure, the first NIR wavelength is 808 nm, the second NIR wavelength is about 780 nm, and the third NIR wavelength is 850 nm.

According to another embodiment of the present disclosure, each of the first, second, and third light sources is a laser diode (LD) or a light emitting diode (LED).

According to one embodiment of the present disclosure, the probe is configured as a tube with the light source disposed at the end of the tube. According to another embodiment of the present disclosure, each of the probe and the detecting means is configured into a pad. According to still another embodiment of the present disclosure, the probe and the detecting means are respectively mounted on a headset and are angularly separated by 180 degrees from each other. In the embodiment, the probe and the detecting means mounted on the headset are respectively coupled with a driving means that drives the probe and the detecting means to move on the headset synchronously in circular motion.

Compared with traditional detecting and imaging technology, the present device is advantageous in that the probe and detecting means can be disposed at different positions (such as head, nose, ear, and mouth of the subject) in accordance with the requirements of application, thereby improving the accuracy and efficiency of measurement.

The second aspect of the present disclosure pertains to a method of determining brain oxygen level in a subject by using the present device. The method comprises,
(a) respectively placing the probe and detecting means on a first and a second sites; wherein the first and second sites are respectively selected from the group consisting of head, nose, ear, and mouth of the subject;
(b) measuring the first, second, and third intensities of the first, second, and third NIR wavelengths after being transmitted across the brain of the subject by each of the first, second, and third NIR detectors of the detecting means; and
(c) determining the brain oxygen level of the subject based on the measured first, second, and third intensities of the step (b) using equations (1) and (2):

$$R_i = \log\left(\frac{I_i}{I_0}\right), i = 1, 2, 3, \quad (1)$$

$$\begin{bmatrix} R_1 \\ R_2 \\ R_3 \end{bmatrix} = \begin{bmatrix} \epsilon^{Hb}(\lambda_1)L & \epsilon^{HbO2}(\lambda_1)L & 1 \\ \epsilon^{Hb}(\lambda_2)L & \epsilon^{HbO2}(\lambda_2)L & 1 \\ \epsilon^{Hb}(\lambda_3)L & \epsilon^{HbO2}(\lambda_3)L & 1 \end{bmatrix} \begin{bmatrix} [Hb] \\ [HbO2] \\ G \end{bmatrix}, \quad (2)$$

wherein $I_0$ and I respectively represent the intensity of NIR wavelength emitted from the light source and the intensity of NIR wavelength measured by the NIR detector, R is the logarithm of the ratio of I and $I_0$, $\lambda$ is the NIR wavelength, $\in$ is an extinction coefficient of Hb or $HbO_2$, L is an optical path length of NIR wavelength, and G is an absorption coefficient.

The brain oxygen level would further provide information to evaluate the localization and mass lesion of brain hematoma. Alternatively, the localization of brain hematoma may be determined directly by analyzing the signal profiles of three NIR wavelengths being transmitted through three pathways with different depths and absorbance. The third aspect of the present disclosure is thus directed to a method for monitoring or detecting a brain hematoma in a subject. The method comprises,
(a) respectively placing the probe and detecting means on a first and a second sites; wherein the first and second sites are respectively selected from the group consisting of head, nose, ear, and mouth of the subject;
(b) measuring the first, second, and third intensities of the first, second, and third NIR wavelengths after being transmitted across the brain of the subject by each of the first, second, and third NIR detectors of the detecting means; and
(c) comparing the first, second, and third intensities of the first, second, and third NIR wavelengths obtained from step (b) with that of a healthy subject, and if the first, second, and third intensities of the first, second, and third NIR wavelengths are different from that of the healthy subject, then the subject has the brain hematoma.

For an accurate measurement, the probe and the detecting means are devised to be disposed on different sites. According to one embodiment of the present disclosure, the probe and the detecting means are respectively disposed in the nose and on the head of the subject. According to another embodiment of the present disclosure, the probe and the detecting means are respectively disposed in the ear and on the head of the subject. According to still another embodiment of the present disclosure, the probe and the detecting means are respectively disposed in the mouth and on the head of the subject.

Many of the attendant features and advantages of the present disclosure will become better understood with reference to the following detail description.

BRIEF DESCRIPTION OF THE DRAWINGS

The present description will be better understood from the following detailed description read in light of the accompanying drawings, where.

Figure 1:
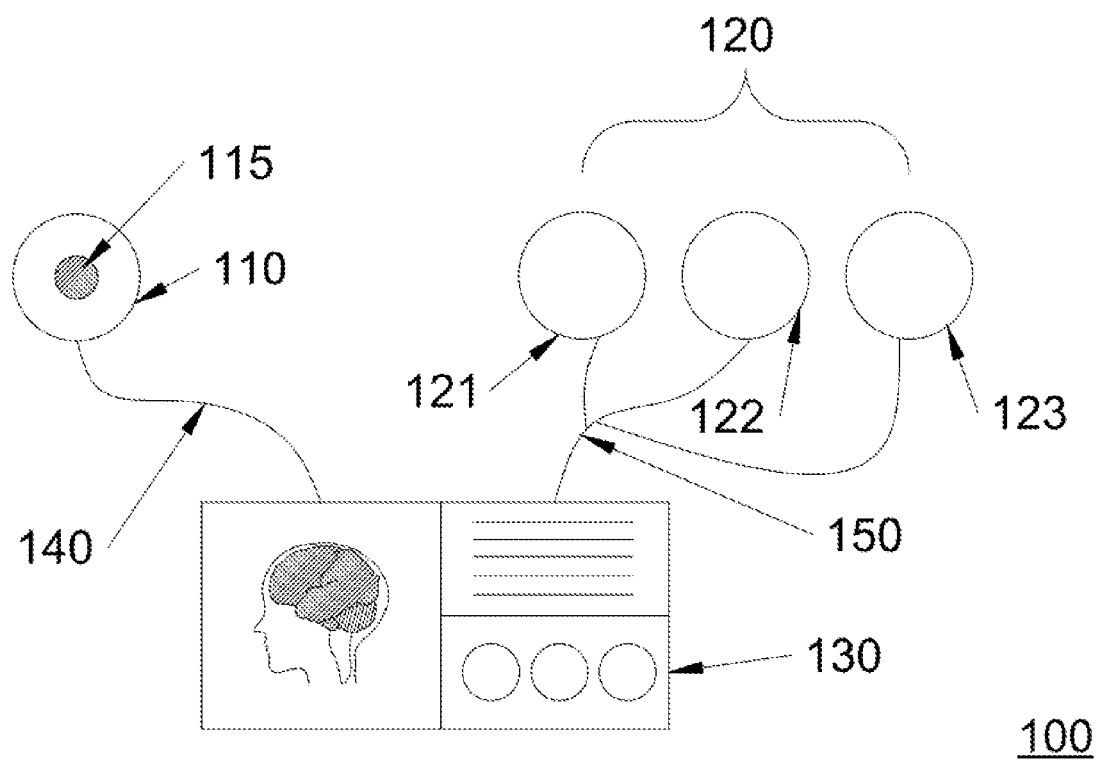
FIG. 1 is a schematic diagram that depicts the device comprising one light source and three NIR detectors according to one embodiment of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts.

DETAILED DESCRIPTION OF PREFERRED EMBODIMENTS

The detailed description provided below in connection with the appended drawings is intended as a description of the present examples and is not intended to represent the only forms in which the present example may be constructed or utilized. The description sets forth the functions of the examples and the sequence of steps for constructing and operating the examples. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

The term "subject" refers to a mammal including the human species that is treatable by the device, and/or methods of the present invention. The term "subject" is intended to refer to both the male and female gender unless one gender is specifically indicated.

The term "near infrared (NIR)" as used herein refers to light in a spectrum ranging from about 650 to about 3,000 nm, more preferably from about 650 to about 1,400 nm, and, most preferably from about 650 to about 1,000 nm.

Red blood cells are the main carrier of the oxygen in the body, thus, the blood oxygen level is determined by how fully saturated the hemoglobin is, by the oxygen molecules present in the blood; or by the ratio of oxy-hemoglobin (HbO$_2$) to deoxy-hemoglobin (Hb). These two types of hemoglobin exhibits different absorption properties in the near infrared wavelengths that penetrate the tissue. Accordingly, it is possible to calculate the concentrations of HbO$_2$ and Hb, and eventually the blood oxygen level, by taking advantage of their NIR properties with algorithms derived from the Beer-Lambert law. The blood oxygen level in a tissue, in turn, can be used as an index to determine if there is an injury in the tissue.

The Beer-Lambert Law is a relationship that maps absorption of light to the properties of the material through which the light is traveling. There are several ways in which the law can be expressed. The transmittance (T) of light through a medium, which is the ratio of the intensity of light that enters a medium ($l_O$) over the intensity of the light that exits the medium ($l_I$) may be expressed as:

$$T = \frac{l_0}{l_i} = e^{-\alpha \cdot l \cdot c},$$

wherein $$\alpha = \frac{4\pi k}{\lambda},$$

$\lambda$ is the wavelength of the light, and k is the extinction coefficient. In terms of absorbance (A) of light:

$$A = \log\frac{l_o}{l_i},$$

and A=$\alpha \cdot l \cdot c$, where l is the distance that the light travels through the material (the path length), c is the concentration of absorbing species in the material, and $\alpha$ is the absorption coefficient or the molar absorptivity of the medium.

The present invention is directed to a device that provides an accurate and efficient measurement of brain oxygen level in a subject. The device of the present invention is operated on the basis of the NIR properties of HbO$_2$ and Hb by taking NIR measurements at multiple locations (such as at least three different locations) in a subject via use of multiple NIR wavelengths. More specifically, in the present device, one of the NIR wavelengths is an isosbestic point for HbO$_2$ and Hb, and the other two wavelengths may be any wavelengths within the near infrared spectrum (about 650 nm to 1000 nm), so long as one wavelength is shorter than the isosbestic point, and the other wavelength is longer than the isosbestic point. The NIR intensities measured at three wavelengths and at three different locations are then applied to algorithms derived from the Beer-Lambert law to generate the saturation degree of tissue oxygenation. From the obtained saturation degree of tissue oxygenation, a physician may then determine the presence or absence of brain hematoma, and preferably, the location of brain hematoma.

Accordingly, the first aspect of the present disclosure pertains to a device for measuring brain oxygen level in a subject having or suspected of having brain hematoma.

Reference is now made to FIG. 1, which is a schematic drawing depicting a device 100 for measuring the brain oxygen level in accordance with one embodiment of the present disclosure. The device 100 comprises a probe 110 and a detecting means 120, respectively coupling to a processor 130. The probe 110 comprises a first light source 115 configured to intermittently emit a first, a second, and a third NIR wavelengths across the brain of the subject; wherein the first NIR wavelength is the isosbestic wavelength for HbO$_2$ and Hb, the second NIR wavelength is shorter than the first NIR wavelength, and the third NIR wavelength is longer than the first NIR wavelength. The detecting means 120 comprises a first NIR detector 121, a second NIR detector 122, and a third NIR detector 123, wherein each of the three NIR detectors is configured to respectively measure the first, second, and third intensities of the first, second, and third NIR wavelengths after being transmitted across the brain of the subject. In the exemplified embodiment, the probe 110 and the detecting means 120 are respectively connected to the processor 130 by a light guide (140, 150) sheathed in plastic, such as polyvinyl chloride (PVC)-covered coils. Alternatively, the probe 110 and the detecting means 120 may be coupled to the processor 130 via a wireless connection, such as, bluetooth, wireless fidelity (WiFi), infrared, ultra-wideband connection, and the like.

Figure 2:
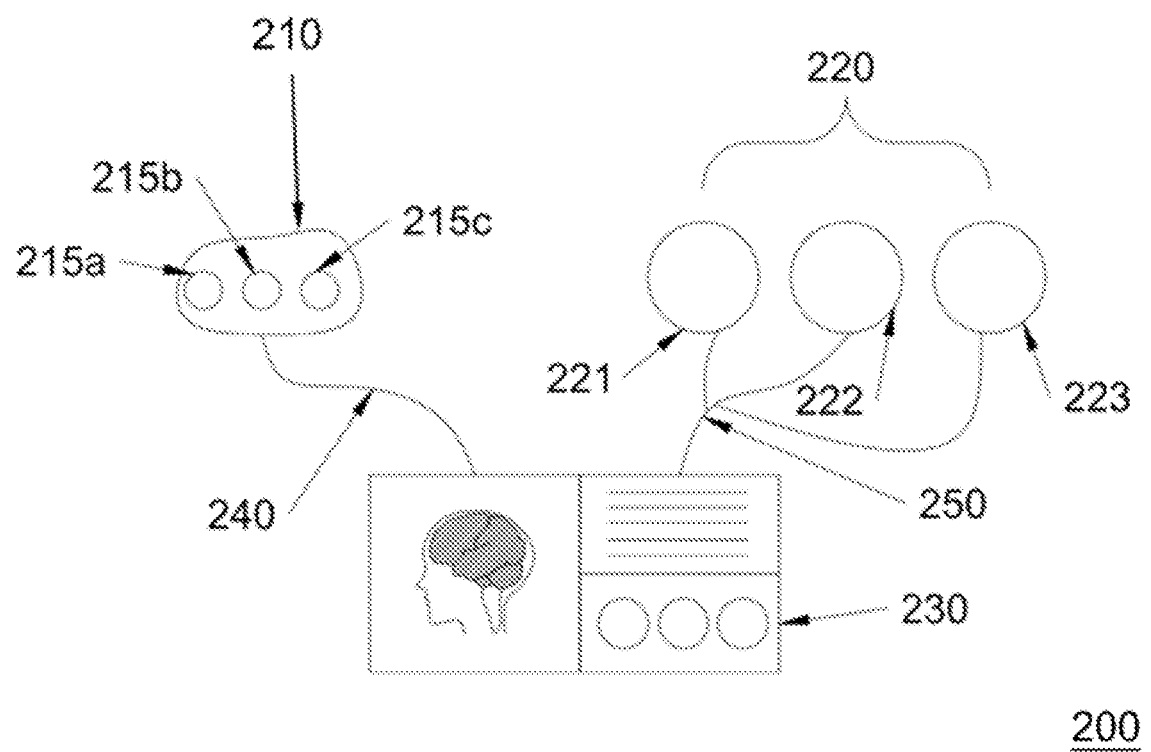
FIG. 2 is a schematic diagram that depicts the device comprising three light sources and three NIR detectors according to another embodiment of the present disclosure.

FIG. 2 depicts another embodiment of the device 200 of the present disclosure, in which three, instead of one, light sources are employed; and the arrangement of the rest of the elements are same as those depict in FIG. 1. The exemplified device 200 comprises a probe 210 and a detecting means 220, respectively coupling to a processor 230. The device 200 is characterized in that the probe 210 comprises a first, a second and a third light sources (215a, 215b, 215c); which are configured to simultaneously emit a first, a second, and a third NIR wavelengths across the brain of the subject. The detecting means 220 comprises a first, a second and a third NIR detectors (221, 222, 223), wherein each of the NIR detectors (221, 222, 223) is configured to respectively measure the first, second, and third intensities of the first, second, and third NIR wavelengths transmitted across the tissue (e.g., the head) of the subject. Similar to the arrangement depicted in FIG. 1, the probe 210 and the detecting means 220 are respectively connected to the processor 230 by a light guide (240, 250) sheathed in plastic (e.g., PVC)-covered coils; or by a wireless connection, which includes, but is not limited to, bluetooth, WiFi, infrared, or ultra-wideband connection.

In the embodiments of the present disclosure, the first NIR wavelength is about 790 nm to 810 nm, the second NIR wavelength is about 650 nm to 790 nm, and the third NIR wavelength is about 810 nm to 1,000 nm. In one specific example, the first NIR wavelength is 808 nm, the second NIR wavelength is about 780 nm, and the third NIR wavelength is 850 nm.

Examples of light source suitable for use in the present device include, but is not limited to, a light emitted diode (LED) and a laser diode (LD), either diode is capable of emitting lights in NIR wavelengths. In a preferred embodiment of the present disclosure, the light sources are LDs, capable of emitting wavelengths range from about 650 nm to about 1,000 nm. According to embodiments of the present disclosure, the output power of each light source is about 5 milliwatts (mW).

In practice, the probe 210 and the detecting means 220 are respectively placed at sites selected from the group consisting of, the head, the nose, the ear, and the mouth, of the subject. In general, the probe 210 and the detecting means 220 are placed at different sites of the subject, such as the probe 210 is disposed in the nose, while the detecting means 220 is disposed on the head. Alternatively, they may be placed on the same site (e.g., both are on the head), provided that they are spaced apart by a pre-designated distance. For example, if both the probe 210 and the detecting means 220 are placed on the head of the subject, they are spaced apart by an angle ranging from 10 to 180 degrees.

In one specific embodiment, upon activation, the light sources (215a, 215b, 215c) disposed on the probe 210 emits a first, a second, and a third NIR wavelengths, respectively across the brain of the subject. The three NIR wavelengths travel across the tissue and are detected by the NIR detectors (221, 222, 223) disposed on the detecting means 220. The detected NIR intensities are then processed by the built-in algorithms in the processor 230, the algorithms are derived from the Beer-Lambert law and are used to calculate the brain oxygen level of the subject. According to embodiments of the present disclosure, the brain oxygen level is determined by equations (1) and (2):

$$R_i = \log\left(\frac{I_i}{I_0}\right), i = 1, 2, 3, \qquad (1)$$

$$\begin{bmatrix} R_1 \\ R_2 \\ R_3 \end{bmatrix} = \begin{bmatrix} \epsilon^{Hb}(\lambda_1)L & \epsilon^{HbO2}(\lambda_1)L & 1 \\ \epsilon^{Hb}(\lambda_2)L & \epsilon^{HbO2}(\lambda_2)L & 1 \\ \epsilon^{Hb}(\lambda_3)L & \epsilon^{HbO2}(\lambda_3)L & 1 \end{bmatrix} \begin{bmatrix} [Hb] \\ [HbO2] \\ G \end{bmatrix}, \qquad (2)$$

wherein $I_0$ and I respectively represent the intensity of NIR wavelength emitted from the light source and the intensity of NIR wavelength measured by the NIR detectors, R is the logarithm of the ratio of I and $I_0$, $\lambda$ is the NIR wavelength, $\in$ is an extinction coefficient of Hb or HbO$_2$, L is an optical path length of NIR wavelength, and G is an absorption coefficient.

Figure 3A:
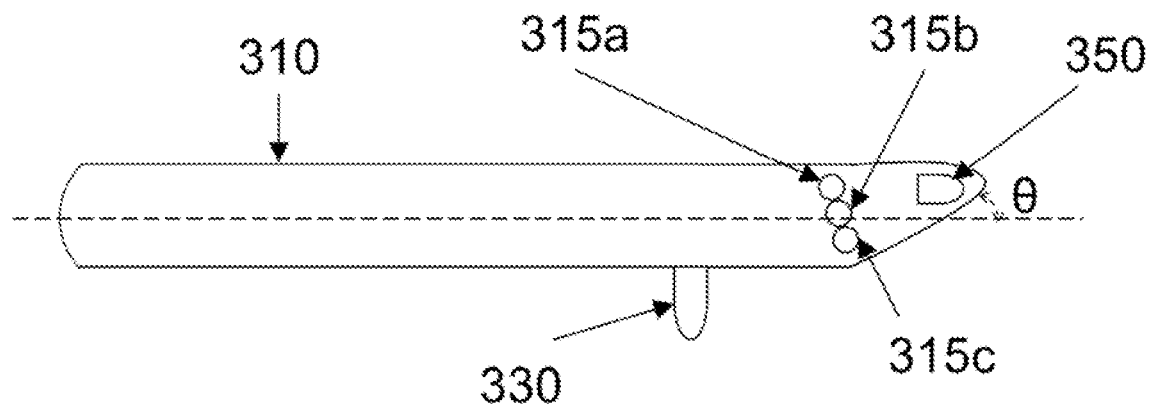
FIG. 3A is a schematic diagram that depicts a probe configured as a tube according to one embodiment of the present disclosure.

In the case when the probe 210 of the present device is placed on sites having a canal-like structure, such as within the nose, the mouth and the ear; then a specialized probe is required for practicing the present invention. Reference is now made to FIG. 3A, which depicts a probe 310 suitable for use in sites like the mouth, the nose and the ear. The probe 310 is in the form of a tube, and comprises three light sources (315a, 315b, 315c) disposed at one end. The probe 310 may be made of a plastic flexible material with flexibility, such as rubber, PVC, polyamide (PA), polyester (PES), polyethylene terephthalate (PET), polyethylene (PE), high-density polyethylene (HDPE), polyvinylidene chloride (PVDC), low-density polyethylene (LDPE), polypropylene (PP), polystyrene (PS), high impact polystyrene (HIPS), polyurethanes (PU) and the like. Alternatively, the probe 310 may be made of silica selected from the group consisting of fused silica glass, soda-lime-silica glass, sodium borosilicate glass, lead-oxide glass, and aluminosilicate glass. The probe 310 may further comprise a spacer element 330 disposed on one side of the outer surface of tube, and close to the end of the tube where the light sources (315a, 315b, 315c) reside. In operation, when the probe 310 is inserted into sites such as the mouth, the ear and the nose, the spacer element 330 may provide additional space to keep the canal structure of the sites from being obstructed. The length of the probe 310 is sufficient enough to allow the probe 310 itself to be inserted into the site, such as into the mouth, the nose and the ear. Typically, the probe 310 has a length ranging from about 5 cm to about 30 cm, such as 5 cm, 10 cm, 15 cm, 20 cm, 25 cm, or 30 cm.

According to one embodiment of the present disclosure, the probe 310 further comprises a camera 350. In the embodiment, the light sources (315a, 315b, 315c) and the camera 350 are disposed at the same end of the probe 310. According to another embodiment of the present disclosure, the end of probe 310, where the camera 350 and the light sources (315a, 315b, 315c) reside, is slanted for easy insertion of the probe 310 into the canal-like structure. In this embodiment, the slanted end is at an angle (θ) of about 45±10 degrees with the longitudinal direction of the probe 310.

Figure 3B:
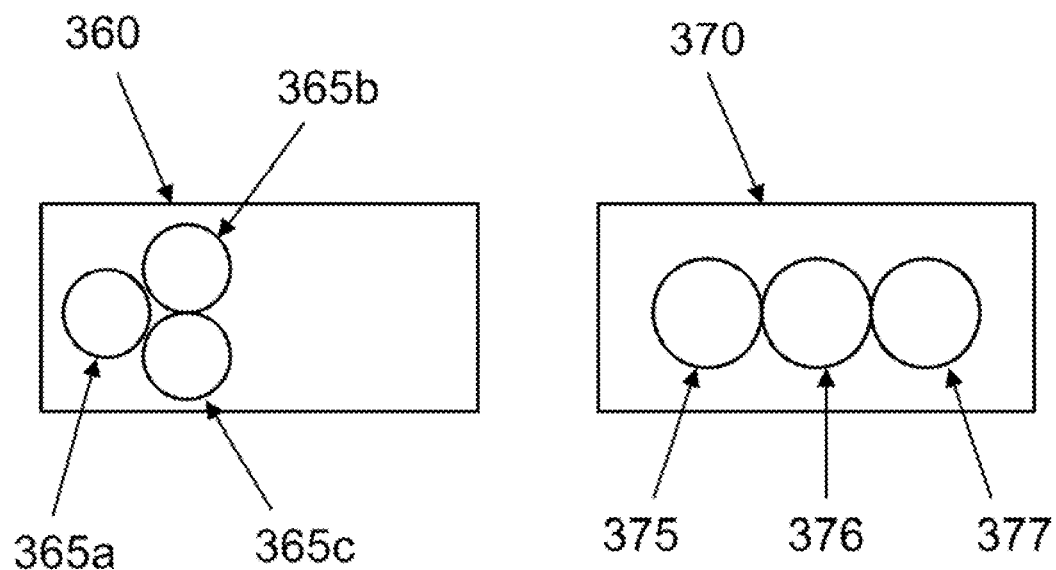
FIG. 3B is a schematic diagram that depicts a probe (left panel) and a detecting means (right panel) respectively configured into pads according to another embodiment of the present disclosure.

FIG. 3B provides an example in which the probe 360 and the detecting means 370 are respectively configured in the form of pads. Each pad is composed of, from top to bottom, a releasing film, an adhesive layer, and a supporting substrate, in which the probe 360 or the detecting means 370 is fixed on the supporting substrate of the pad by the adhesive layer. During operation, a user tears away the releasing film to expose the three light sources (365a, 365b, 365c) or the three NIR detectors (375, 376, 377) fixed on the supporting substrate by the adhesive layer, then the pad is secured to the intended site (e.g., the head) by pressing the side of the adhesive layer against the intended site. According to the embodiments of the present disclosure, the pad may be made of any conventional material, preferably, made of resilient polyurethane, natural or synthetic rubber, or fabric.

Figure 4:
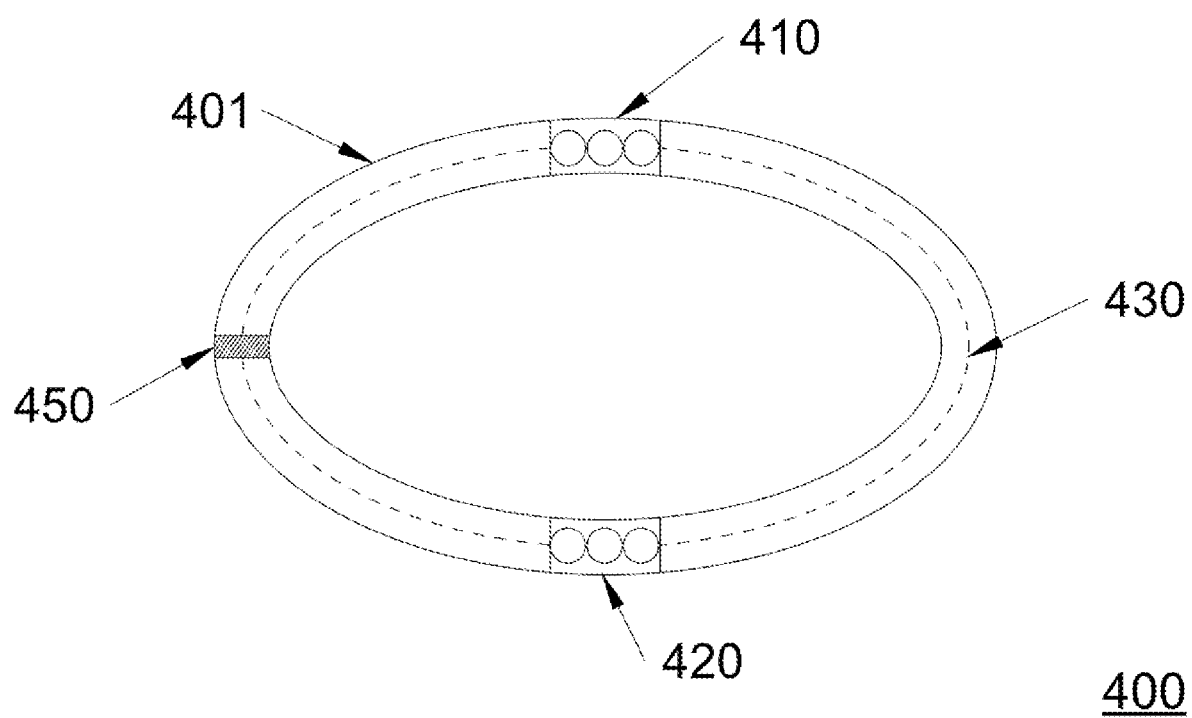
FIG. 4 is a schematic diagram that depicts the configuration of the device, wherein both of the probe and the detecting means are mounted on a headset according to the embodiment of the present disclosure.

In other embodiments of the present disclosure, both the probe and the detecting means of the present device (100 or 200) are configured into a headset for wearing on the head of the subject. Reference is now made to FIG. 4. The headset 400 comprises a track-like structure 401 for mounting the probe 410 and the detecting means 420 thereon, in which the probe 410 and the detecting means 420 are spaced apart by 180 degrees; and a driving means 430 coupled to the probe 410 and the detecting means 420 for driving the probe 410 and the detecting means 420 to move synchronously on the track-like structure 401 in circular motion. The headset 400 may be made of a material that is plastic or metal. Preferably, the headset 400 is hollow in structure so as to reduce the weight of the headset. Optionally, the headset 400 further comprises a securing means 450 that allows the user to adjust the size of the headset 400 according to his/her respective needs during the operation. The securing means 450 may be a strip made of an elastic material, a hook, or a loop fastener (e.g., Velcro™).

Since a mass lesion would interfere the transmission of NIR wavelengths, the present device is also aimed to provide a means for monitoring the brain hematoma. Specifically, the brain hematoma can be detected by evaluating the signal profiles of the first, second, and third NIR intensities transmitted across the brain. Accordingly, another aspect of the present disclosure pertains to a method of monitoring or detecting a brain hematoma in a subject by using the present device as described above. The method comprises, (a) respectively placing the probe and detecting means on a first and a second sites; wherein the first and second sites are respectively selected from the group consisting of head, nose, ear, and mouth of the subject;

(b) measuring the first, second, and third intensities of the first, second, and third NIR wavelengths after being transmitted across the brain of the subject by each of the first, second, and third NIR detectors of the detecting means; and (c) comparing the first, second, and third intensities of the first, second, and third NIR wavelengths obtained from step (b) with that of a healthy subject, and if the first, second, and third intensities of the first, second, and third NIR wavelengths are different from that of the healthy subject, then the subject has the brain hematoma.

Figure 5:
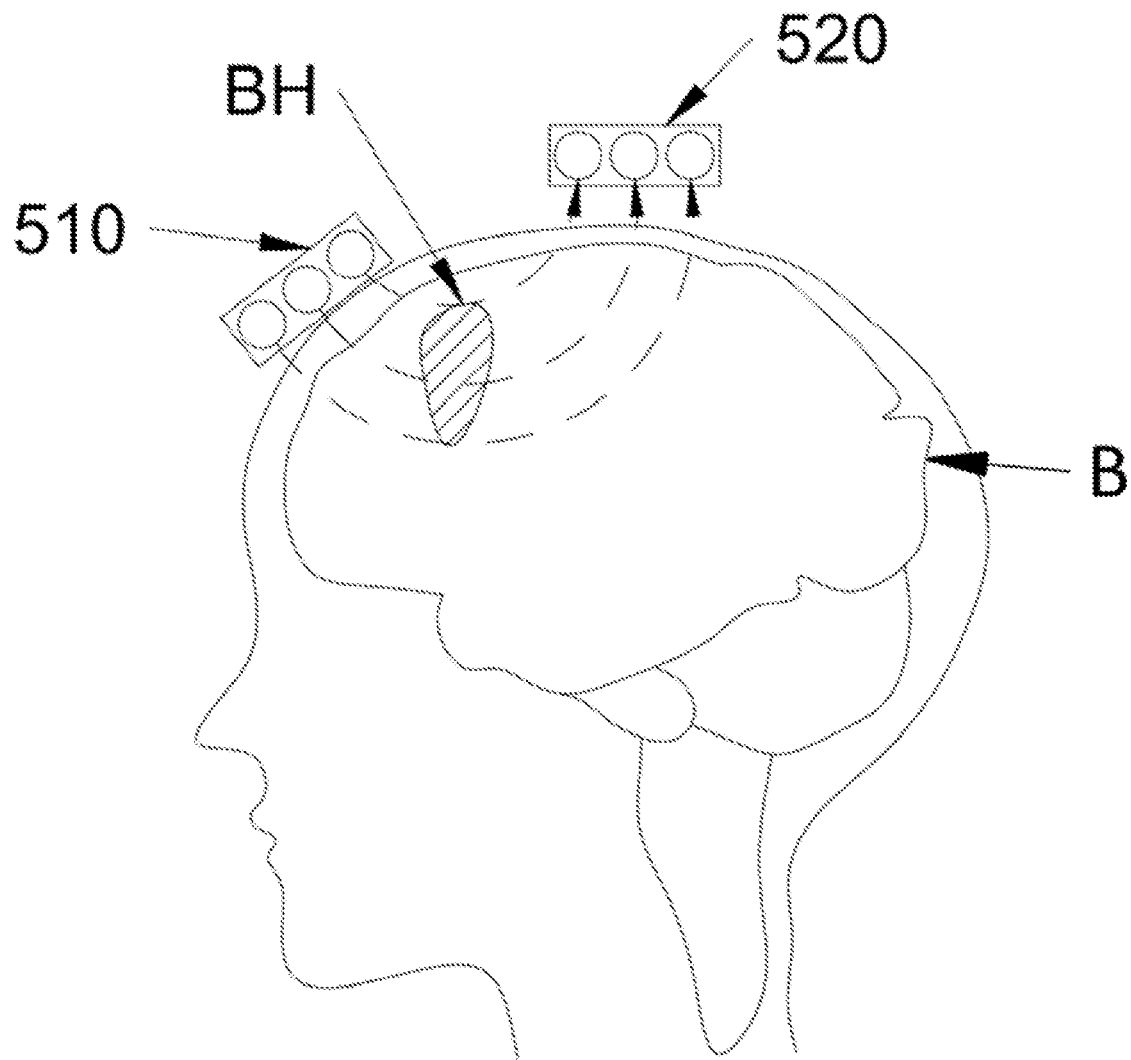
FIG. 5 is a schematic diagram that depicts a method of detecting brain hematoma (BH), wherein the probe and the detecting means are respectively disposed on the forehead and the anterior part of the head, wherein B stands for brain according to one embodiment of the present disclosure.

The selection of suitable first and second sites for placing the probe and detecting means of the present device may be determined by the attending physician and/or operator based on the age, history and current disease condition of the subject. As depicted in the example of FIG. 5, to detect the brain hematoma (BH) close to premotor area, primary motor cortex, or primary somesthetic cortex, the probe 510 and the detecting means 520 are preferably disposed on the forehead and the anterior part of the head of the subject, respectively.

Figure 6:
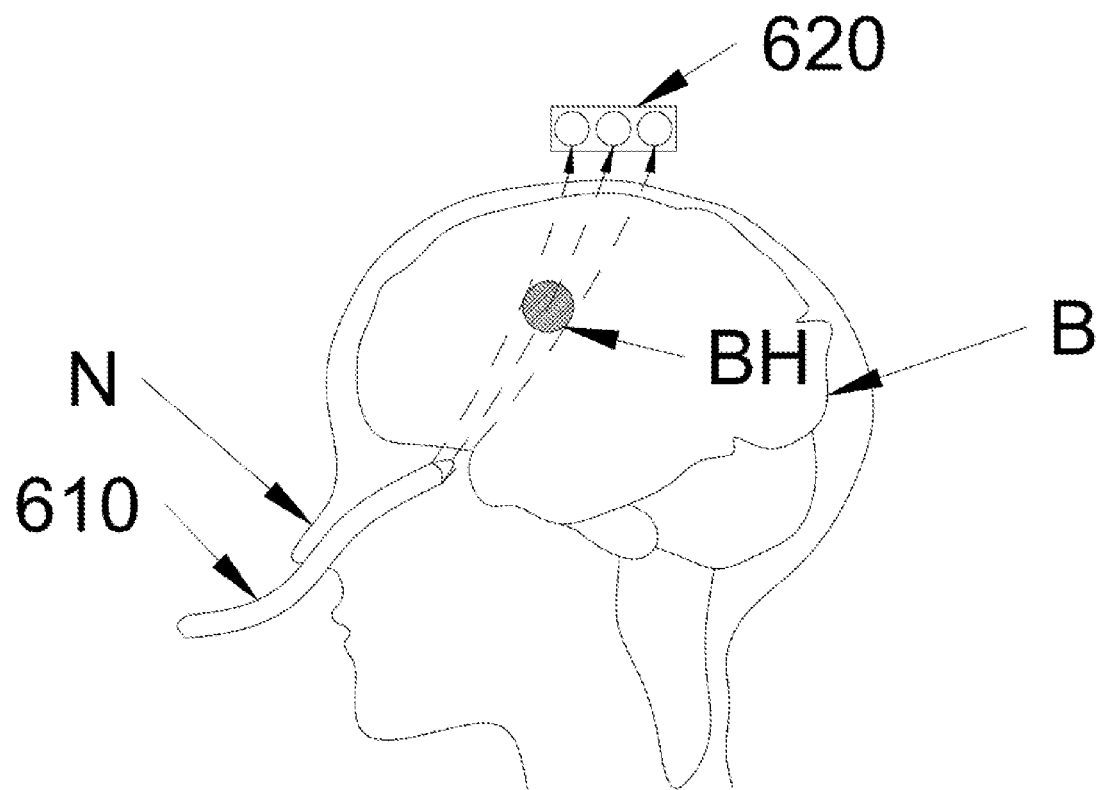
FIG. 6 is a schematic diagram that depicts a method of detecting brain hematoma (BH), wherein the probe and the detecting means are respectively disposed in the nose (N) and on the anterior part of the head, wherein B stands for brain according to one embodiment of the present disclosure.

In another example depicted in FIG. 6, to detect the brain hematoma (BH) near Broca's area, the probe 610 configured as a tube, is inserted into the nose, while the detecting means 620 configured as a pad, is disposed on the anterior part of the head of the subject). In still further example, the probe 610 may be inserted into the nose, while the detecting means 620 is disposed on the posterior part of the head of the subject, so as to monitor the BH around somesthetic association area or Wernicke's area.

Figure 7:
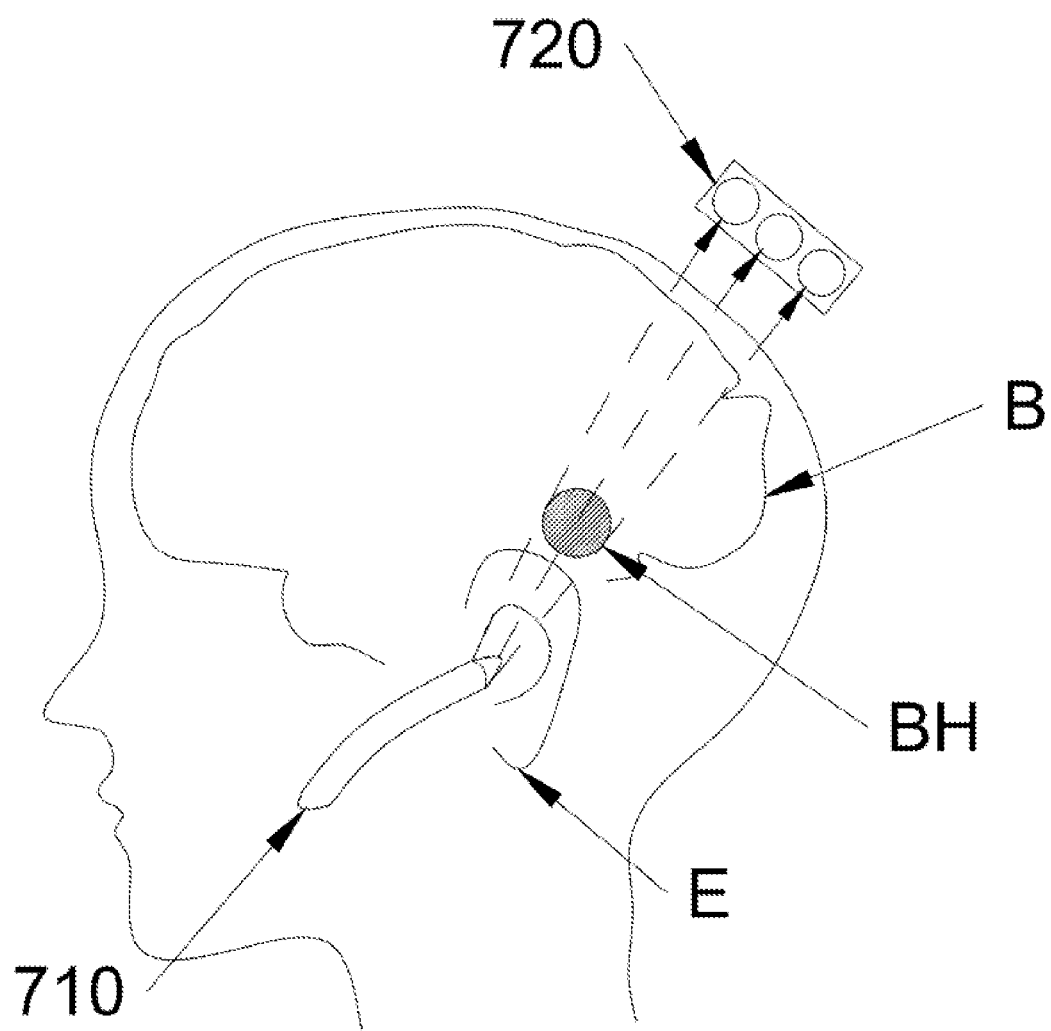
FIG. 7 is a schematic diagram that depicts a method of detecting brain hematoma (BH), wherein the probe and the detecting means are respectively disposed in the ear (E) and on the posterior part of the head, wherein B stands for brain according to yet another embodiment of the present disclosure.

Similarly, as depicted in FIG. 7, the probe 710, configured as a tube, is inserted into the ear, while the detecting means 720, configured as a pad, is disposed on the posterior part of the head of the subject, so as to monitor BH occurs at primary auditory cortex or taste area.

Figure 8:
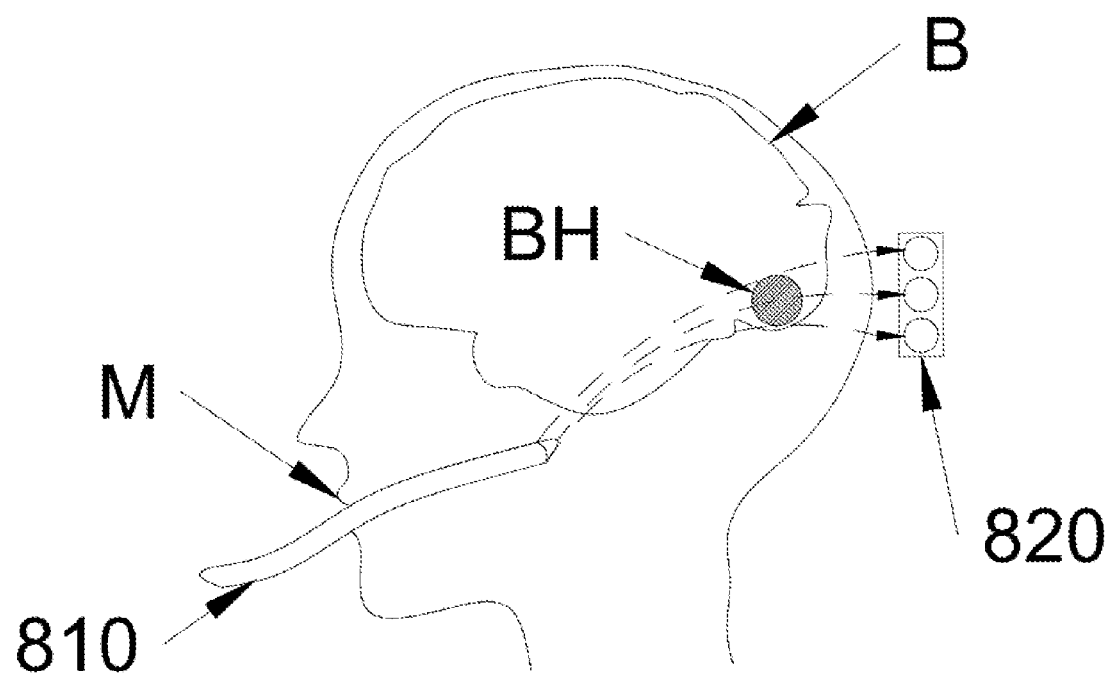
FIG. 8 is a schematic diagram that depicts a method of detecting brain hematoma (BH), wherein the probe and the detecting means are respectively disposed in the mouth (M) and on the occipital part of the head, wherein B stands for brain according to still another embodiment of the present disclosure.

In still another example, as depicted in FIG. 8, the probe 810, configured as a tube, may be disposed in the mouth, while the detecting means 820, configured as a pad, is disposed on the occipital part of the head of the subject, so as to detect BH occurs near visual association area or visual cortex.

The present invention will now be described more specifically with reference to the following embodiments, which are provided for the purpose of demonstration rather than limitation.

EXAMPLES 1.1 Simulation of BH by Use of Embedded Ink Stick

In the examples, an ink stick (1 cm$^3$: 0.65 cm×0.9 cm×1.7 cm; 2.5 cm$^3$: 1.63 cm×0.9 cm×1.7 cm; or 5 cm$^3$: 3.25 cm×0.9 cm×1.7 cm) embedded in a plastic article made of titanium oxide and polyester resin (the distance between the ink stick and the surface of plastic article was 0.5 cm, 1.7 cm, or 2.5 cm) was used to imitate different situations of brain hematoma (BH, with different mass lesions and locations). The probe was set to emit NIR respectively at 808 nm, 780 nm, and 850 nm. During operation, the probe and the detecting means were respectively disposed on either the same sides (as traditional detecting method, in which the light source and detector were configured closely and operated in proximity to each other), or on the opposite sides of the plastic article (i.e., the simulated BH). Results obtained from the same and opposite sides are respectively provided in FIGS. 9 and 10.

Figure 9A:
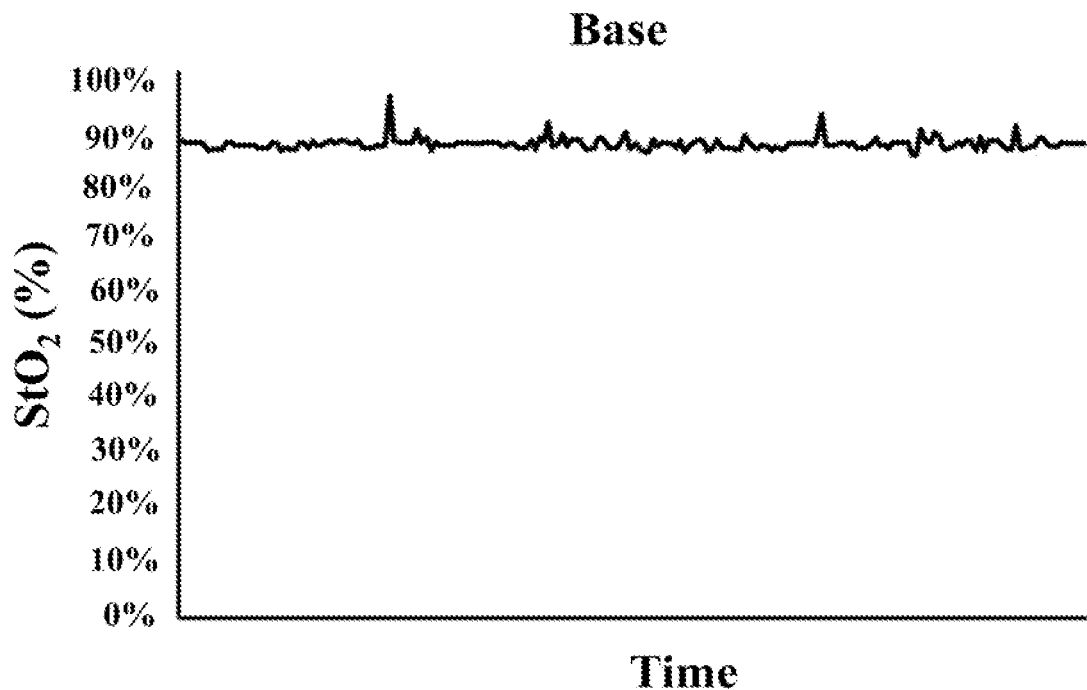
FIGS. 9A-9D are the oxygen level of plastic article having the ink stick of 0 cm$^3$ (Base, FIG. 9A) or 5 cm$^3$ embedded at specified depth (FIGS. 9B-9D) according to one embodiment of the present disclosure.
Figure 9B:
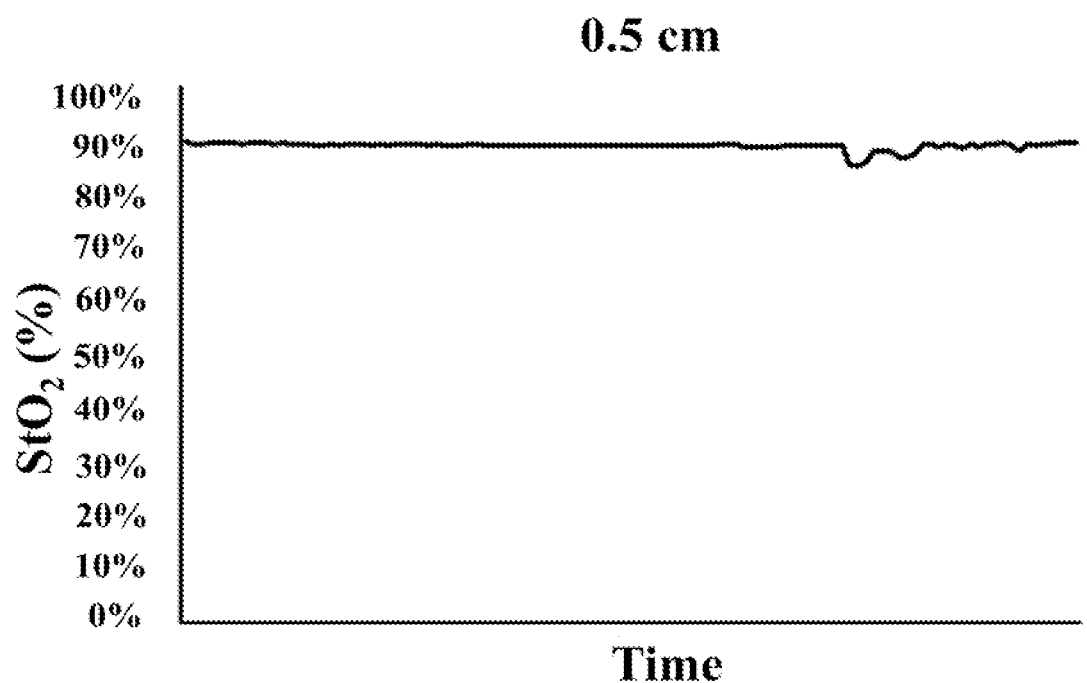
Figure 9C:
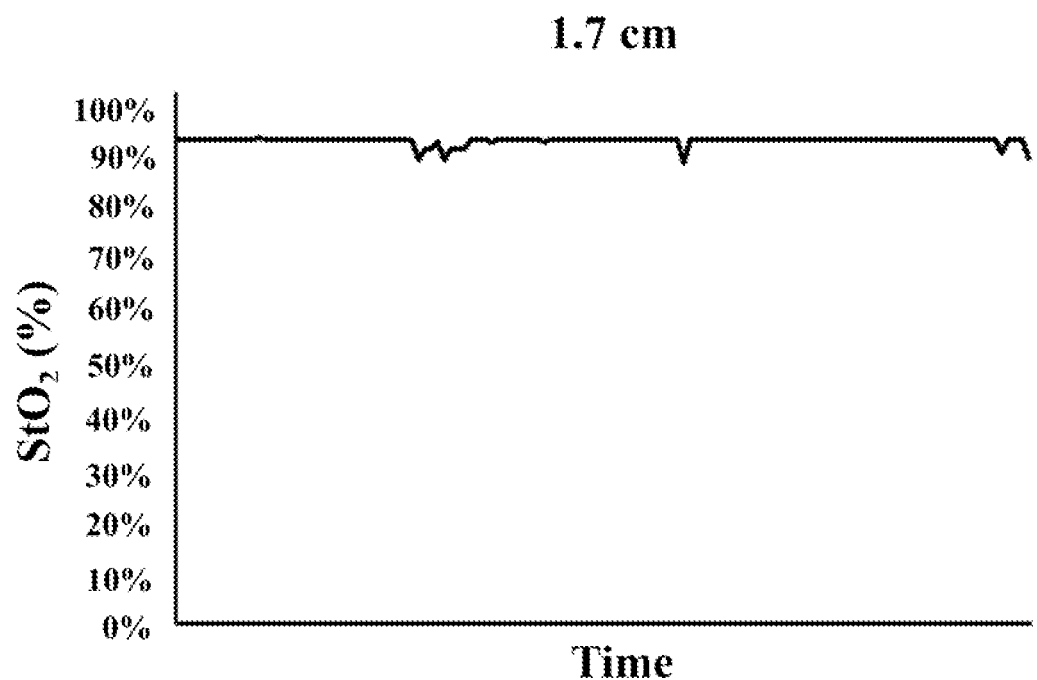
Figure 9D:
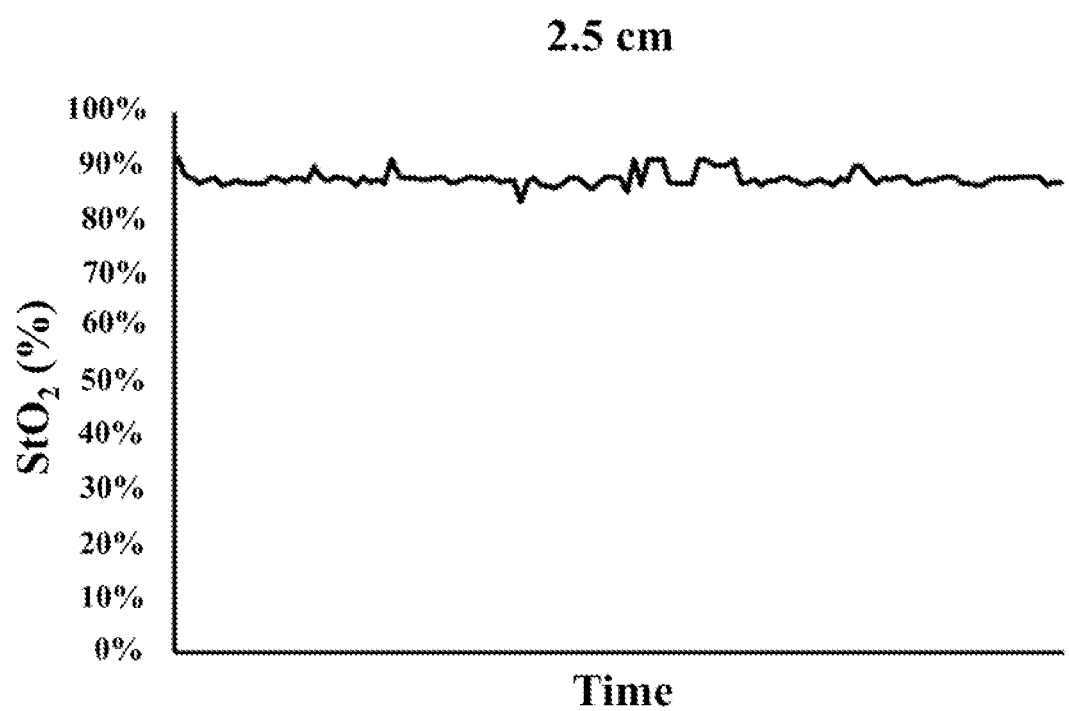
Figure 10A:
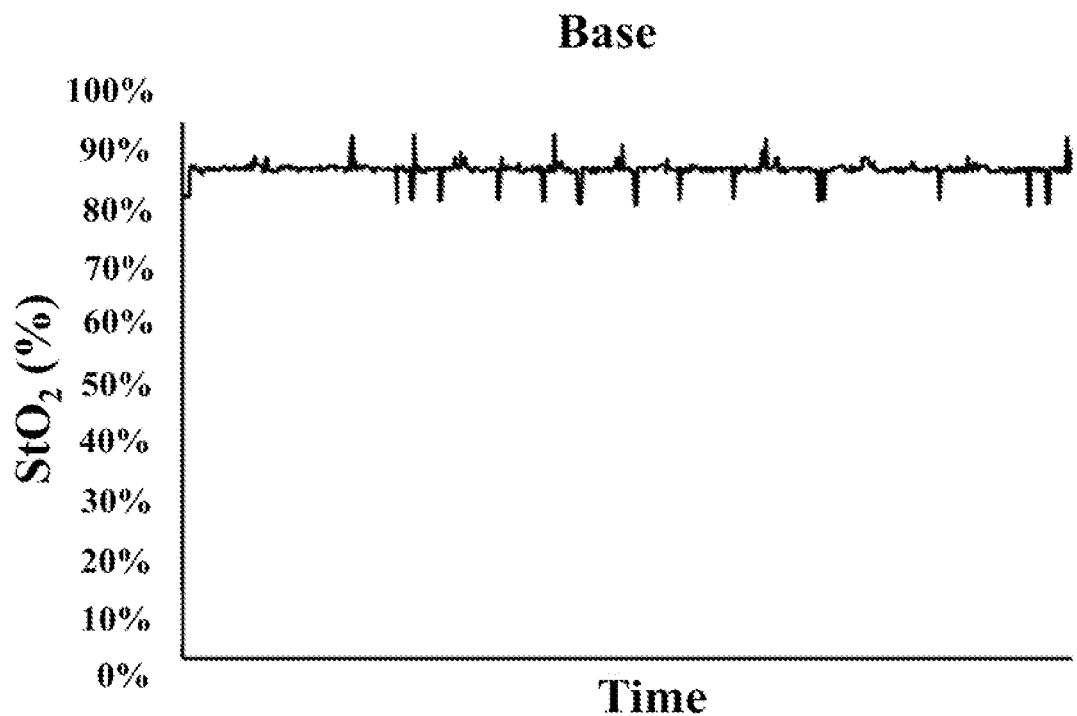
FIGS. 10A-10D are the oxygen level of plastic article having the ink stick of 0 cm$^3$ (Base, FIG. 10A) or 5 cm$^3$ embedded at specified depth (FIGS. 10B-10D) according to another embodiment of the present disclosure.
Figure 10B:
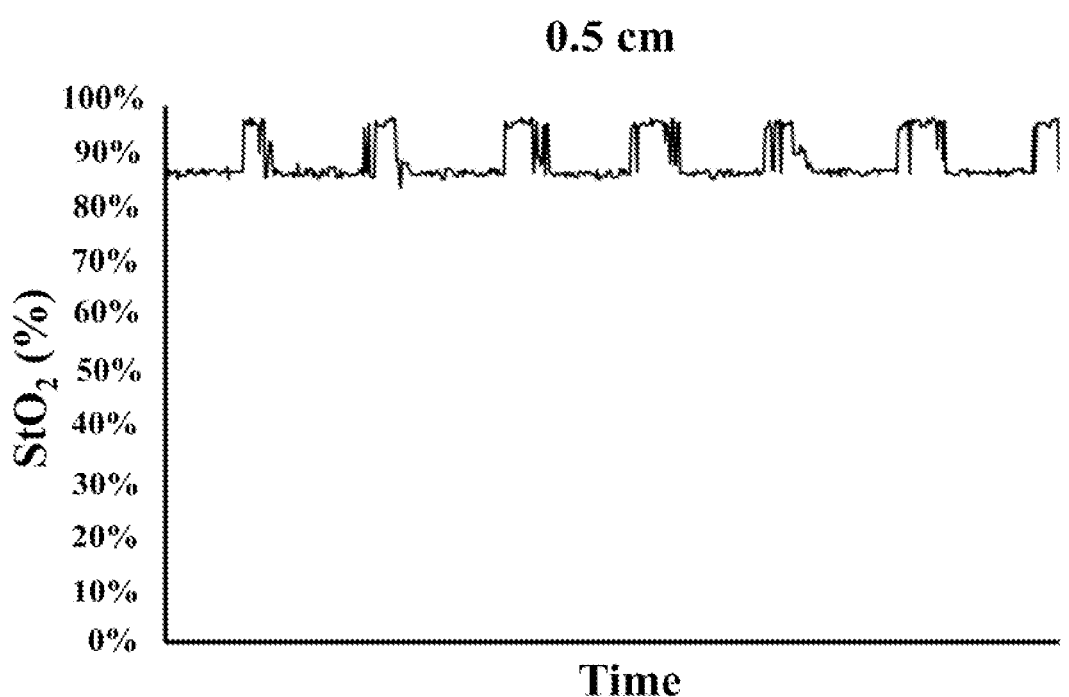
Figure 10C:
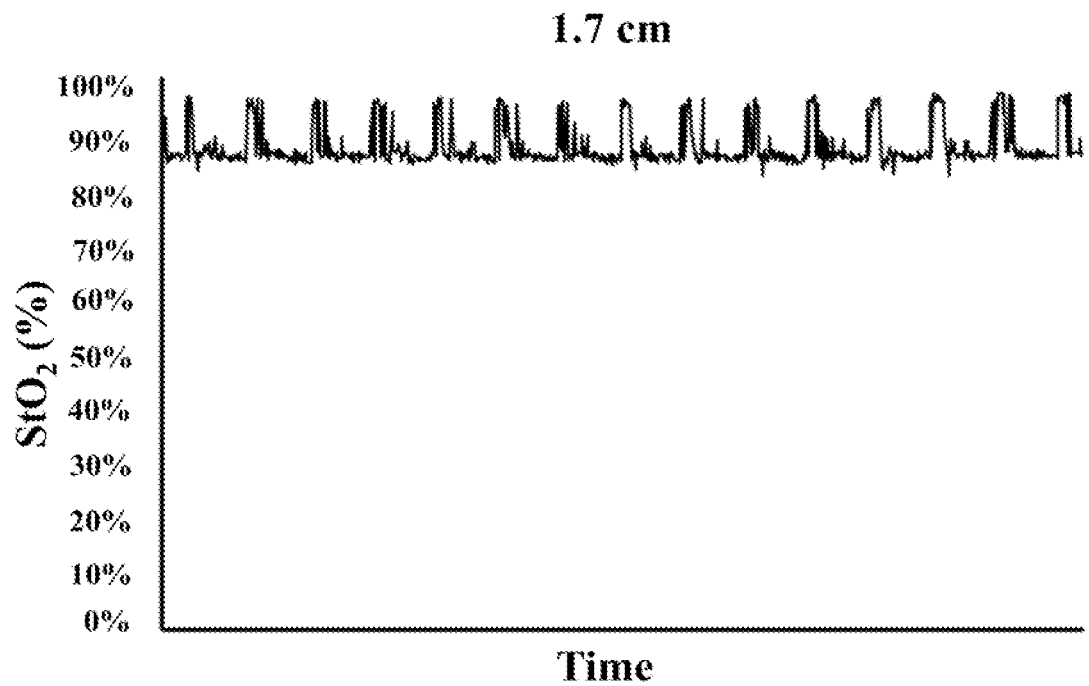
Figure 10D:
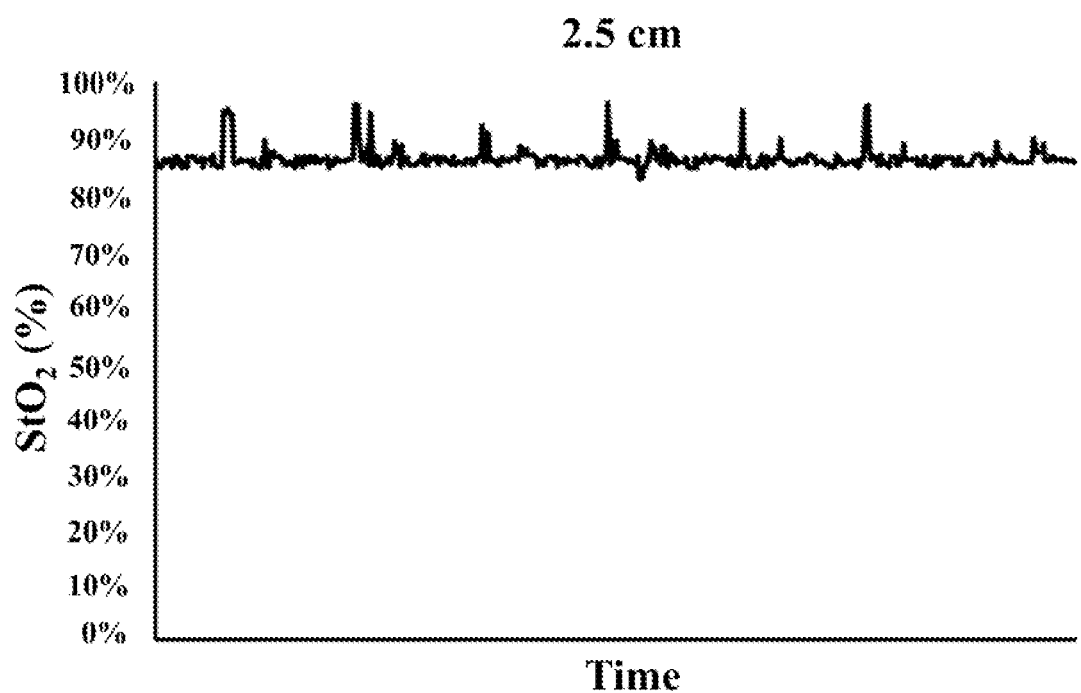

When the probe was disposed in close proximity to the detecting means, no significant difference was found between the control group (that is, without the ink stick embedded therein, designated as Base; FIG. 9A) and the imitation groups (that is, having embedded ink stick at the specified depth; FIGS. 9B to 9D). By contrast, when the probe and the detecting means were disposed at opposite sides of the plastic article (i.e., the simulated BH site), the signal profiles varied with the embedded depth of the ink stick (FIGS. 10B to 10D), as compared with the control group (designated as Base; FIG. 10A). The results indicated that compared with traditional detecting method, in which the measurement was limited by the configuration of light source and detector, the present device and method, in which the probe and detecting means could be operated independently along with varied distance, may provide a more accurate estimation on the brain hematoma occurred at various depths.

The detected NIR intensities were analyzed and presented as oxygen level, and are summarized in Table 1, in which the probe and the detecting means were disposed on the opposite sides of the plastic article. The average oxygen level of plastic article (with specified mass lesion and location) was about 86.74%-91.05%.

TABLE 1

Average oxygen level of specified condition

| Volume (cm³) | Depth (cm) | Average oxygen level |
|---|---|---|
| 0 | 0 | 86.74% |
| 5 | 0.5 | 88.47% |
| 5 | 1.7 | 91.05% |
| 5 | 2.5 | 87.70% |
| 2.5 | 0.5 | 87.74% |
| 2.5 | 1.7 | 87.23% |
| 2.5 | 2.5 | 89.86% |
| 1 | 0.5 | 89.08% |
| 1 | 1.7 | 87.72% |
| 1 | 2.5 | 90.42% |

1.2 Detection of Ink Stick Simulated BH in Pig Head

Figure 11A:
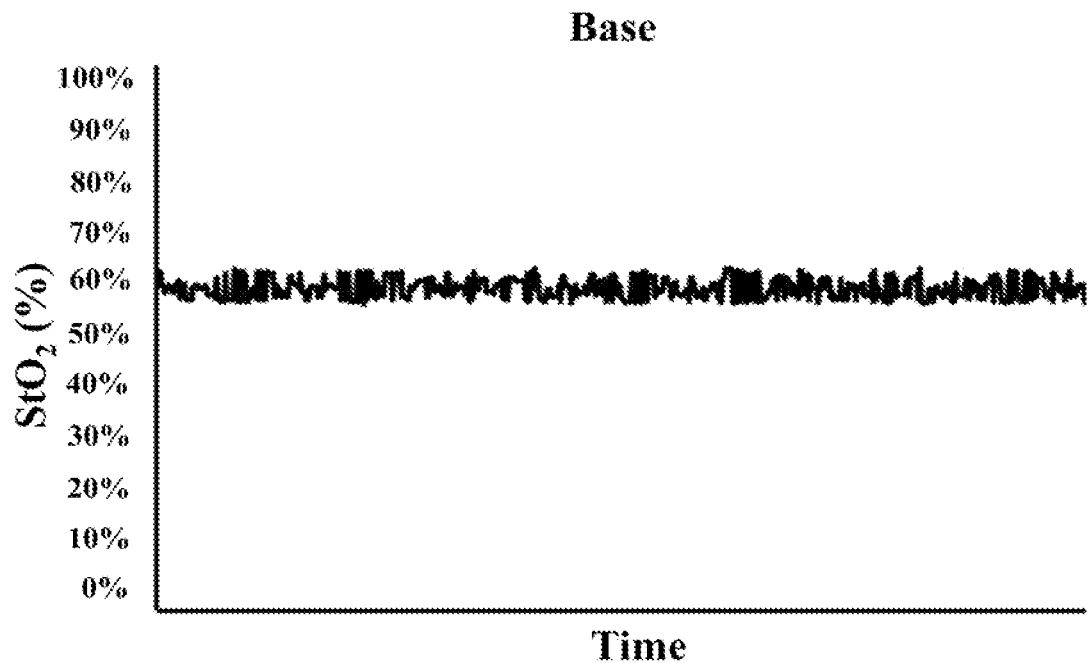
FIGS. 11A-11D are the brain oxygen level of pig's head having the ink stick of 0 cm$^3$ (FIG. 11A), 1 cm$^3$ (FIG. 11B), 2.5 cm$^3$ (FIG. 11C) or 5 cm$^3$ (FIG. 11D) embedded in the temporal lobe according to one embodiment of the present disclosure.
Figure 11B:
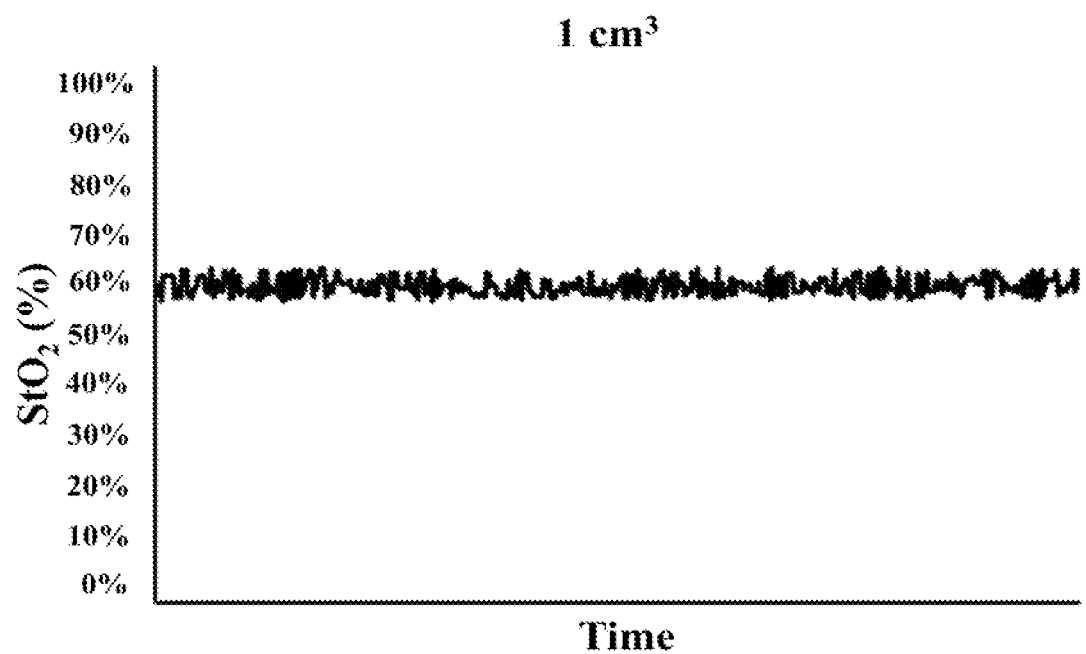
Figure 11C:
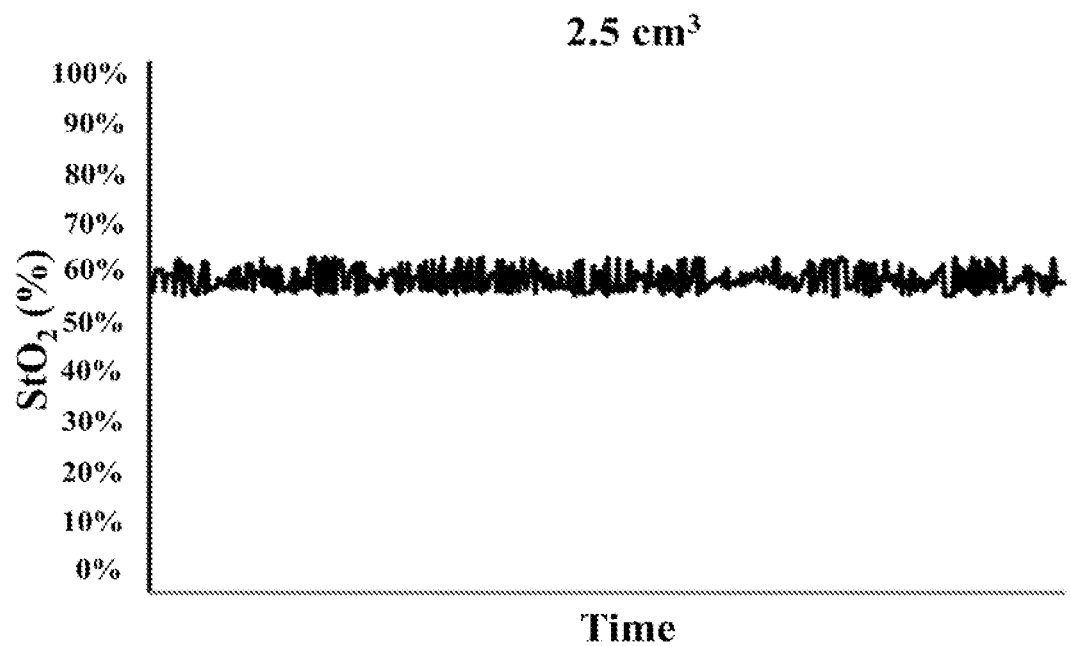
Figure 11D:
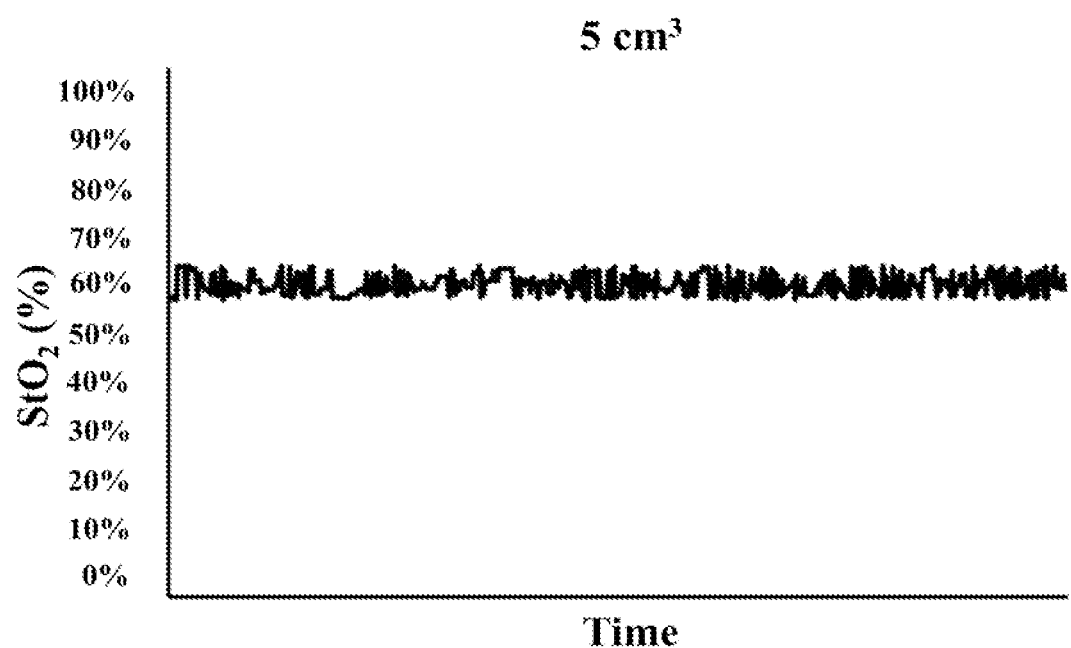

In this example, the ink stick (1 cm³, 2.5 cm³, or 5 cm³) of example 1 was embedded in the temporal lobe of a pig's head so as to imitate the BH in the subject. The probe 310 as depicted in FIG. 3A was inserted into the nose of the pig's head, and the detecting means 370 as depicted in FIG. 3B was disposed on the head. Detection wavelengths were set at 808 nm, 780 nm, and 850 nm. The data depicted in FIG. 11 indicates that the brain oxygen level in the pig's heads having the ink stick of 0 cm³ (FIG. 11A, as healthy control), 1 cm³ (FIG. 11B), 2.5 cm³ (FIG. 11C), or 5 cm³ (FIG. 11D) embedded therein, were respectively about 56-63%.

In conclusion, the present disclosure provided a device and a method for determining the brain oxygen level or monitoring the brain hematoma in a subject. Compared with traditional detecting and imaging technology, the present device is advantageous in that the light source and the detector could be independently operated by placing them at suitable sites to detect brain hematoma, depending on the situation. Accordingly, the present disclosure provides a more accurate and efficient way for detecting the brain oxygen level and/or brain hematoma; and hence, a proper and prompt treatment may thus be provided to the patient in need thereof.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A device for determining brain oxygen level and/or monitoring a brain hematoma in a subject, comprising,
a probe comprising a first, a second, and a third light sources configured to respectively emit a first, a second, and a third near infrared (NIR) wavelengths across the brain of the subject simultaneously, wherein the first, second and third NIR wavelengths are respectively about 790-810 nm, 650-790 nm, and 810-1,000 nm;
a detecting means comprising a first, a second, and a third NIR detectors, wherein each of the NIR detectors is configured to respectively measure a first, a second, and a third intensities of the first, second, and third NIR wavelengths after being transmitted across the brain of the subject;
a processor coupled to the probe and the detecting means, and is configured to determine the brain oxygen level or analyze the brain hematoma based on the first, second, and third intensities detected by the detecting means; and
a headset for wearing on the head of the subject, comprising,
a circular track-like structure for mounting the probe and the detecting means thereon, wherein the probe and the detecting means are disposed at opposite sides of the circular track-like structure thereby are spaced apart by 180 degrees; and
a driving means disposed on the circular track-like structure and coupled to the probe and the detecting means for driving the probe and the detecting means to move synchronously on the circular track-like structure in a direction that is parallel to the headset.

2. The device of claim 1, wherein the first, second and third NIR wavelengths are respectively set at about 808 nm, 780 nm, and 850 nm.

3. The device of claim 1, wherein each of the first, second, and third light sources is a laser diode (LD) or a light emitting diode (LED).

4. The device of claim 1, wherein the probe is in the form of a tube with the first, second, and third light sources disposed at one end therein.

5. The device of claim 1, wherein the brain oxygen level is determined by equations (1) and (2), $$R_i = \log\left(\frac{I_i}{I_0}\right), i = 1, 2, 3, \quad (1)$$

$$\begin{bmatrix} R_1 \\ R_2 \\ R_3 \end{bmatrix} = \begin{bmatrix} \epsilon^{Hb}(\lambda_1)L & \epsilon^{HbO2}(\lambda_1)L & 1 \\ \epsilon^{Hb}(\lambda_2)L & \epsilon^{HbO2}(\lambda_2)L & 1 \\ \epsilon^{Hb}(\lambda_3)L & \epsilon^{HbO2}(\lambda_3)L & 1 \end{bmatrix} \begin{bmatrix} [Hb] \\ [HbO2] \\ G \end{bmatrix}, \quad (2)$$

wherein $I_0$ and I respectively represent an intensity of NIR wavelength emitted from the light source and the intensity of NIR wavelength measured by the NIR detector, R is a logarithm of a ratio of I and $I_0$, $\lambda$ is the NIR wavelength, $\in$ is an extinction coefficient of Hb or $HbO_2$, L is an optical path length of the NIR wavelength, and G is an absorption coefficient.

6. The device of claim 1, wherein the headset is configured to be adjustably fit on the head of the subject.

7. A method of determining brain oxygen level in a subject by using the device of claim 1, comprising:
(a) placing the headset on the head of the subject;
(b) measuring the first, second, and third intensities of the first, second, and third NIR wavelengths after being transmitted across the brain of the subject by each of the first, second, and third NIR detectors of the detecting means; and
(c) determining the brain oxygen level of the subject based on the measured first, second, and third intensities of the step (b) using equations (1) and (2):

$$R_i = \log\left(\frac{I_i}{I_0}\right), i = 1, 2, 3, \quad (1)$$

$$\begin{bmatrix} R_1 \\ R_2 \\ R_3 \end{bmatrix} = \begin{bmatrix} \epsilon^{Hb}(\lambda_1)L & \epsilon^{HbO2}(\lambda_1)L & 1 \\ \epsilon^{Hb}(\lambda_2)L & \epsilon^{HbO2}(\lambda_2)L & 1 \\ \epsilon^{Hb}(\lambda_3)L & \epsilon^{HbO2}(\lambda_3)L & 1 \end{bmatrix} \begin{bmatrix} [Hb] \\ [HbO2] \\ G \end{bmatrix}, \quad (2)$$

wherein $I_0$ and I respectively represent an intensity of NIR wavelength emitted from the light source and the intensity of NIR wavelength measured by the NIR detector, R is a logarithm of a ratio of I and $I_0$, $\lambda$ is the NIR wavelength, $\in$ is an extinction coefficient of Hb or $HbO_2$, L is an optical path length of NIR wavelength, and G is an absorption coefficient.

8. A method of monitoring a brain hematoma in a subject by using the device of claim 1, comprising:

(a) placing the headset on the head of the subject;

(b) measuring the first, second, and third intensities of the first, second, and third NIR wavelengths after being transmitted across the brain of the subject by each of the first, second, and third NIR detectors of the detecting means; and (c) comparing the measured first, second, and third intensities of the first, second, and third NIR wavelengths obtained from the step (b) with those of a healthy subject, and if the measured first, second, and third intensities of the first, second, and third NIR wavelengths are different from those of the healthy subject, then the subject has the brain hematoma.

9. The method of claim 8, wherein the brain hematoma is located at the basal ganglia, the frontal lobe, the parietal lobe, the occipital lobe, the temporal lobe, or the cerebellum.

\* \* \* \* \*